United States Patent [19]
Ovil

[11] Patent Number: 5,690,654
[45] Date of Patent: Nov. 25, 1997

[54] SURGICAL IMPLEMENT PARTICULARLY USEFUL FOR IMPLANTING PROSTHETIC HEART VALVES AND SURGICAL METHOD INCLUDING SUCH IMPLEMENT

[75] Inventor: Joel Ovil, Ramat Hasharon, Israel

[73] Assignee: S.M.T. (Medical Technologies) Ltd., Tel-Aviv, Israel

[21] Appl. No.: 640,149

[22] Filed: Apr. 30, 1996

[30] Foreign Application Priority Data

Jan. 24, 1996 [IL] Israel ............................................ 116891

[51] Int. Cl.⁶ ............................................................ A61B 17/00
[52] U.S. Cl. ................................................ 606/148; 623/900
[58] Field of Search ........................................ 606/148, 139, 606/1; 623/2, 900

[56] References Cited

U.S. PATENT DOCUMENTS

| | | |
|---|---|---|
| 2,588,589 | 3/1952 | Tauber . |
| 2,692,599 | 10/1954 | Creelman . |
| 4,185,636 | 1/1980 | Gabbay et al. . |
| 4,492,229 | 1/1985 | Grunwald . |
| 4,702,250 | 10/1987 | Ovil . |
| 4,932,965 | 6/1990 | Phillips . |
| 5,207,703 | 5/1993 | Jain . |
| 5,304,184 | 4/1994 | Hathaway et al. .......................... 606/148 |
| 5,306,296 | 4/1994 | Wright et al. . |
| 5,439,467 | 8/1995 | Benderev et al. . |
| 5,443,502 | 8/1995 | Caudillo et al. . |
| 5,569,300 | 10/1996 | Redmon .............................. 606/207 |

FOREIGN PATENT DOCUMENTS

| | | | |
|---|---|---|---|
| 1736446 | 5/1992 | U.S.S.R. ................................ | 606/148 |
| 2181950 | 5/1987 | United Kingdom ................. | 606/148 |

*Primary Examiner*—Jeffrey A. Schmidt
*Attorney, Agent, or Firm*—Benjamin J. Barish

[57] ABSTRACT

A surgical implement particularly useful for implanting a prosthetic valve in an excised annulus includes a manually grippable handle, and a suture retainer carried by the handle and having an outer face carrying a coiled spring whose coils define an annular array of slits each having opposed yielding surfaces for receiving and releasably retaining sutures between selected coils. Optimum spacing of the sutures according to the shape of the excised annulus is attained by providing reference ribs between selected coils of the spring, and also by making the outer annular face of the suture retainer of substantially the same shape as that of the excised annulus. Embodiments are also described including an illuminating device for artificially illuminating the working area. Also described is a method of implanting a prosthetic valve in a quick and efficient manner using such an implement.

24 Claims, 4 Drawing Sheets

SURGICAL IMPLEMENT PARTICULARLY USEFUL FOR IMPLANTING PROSTHETIC HEART VALVES AND SURGICAL METHOD INCLUDING SUCH IMPLEMENT

FIELD AND BACKGROUND OF THE INVENTION

The present invention relates to a surgical implement particularly useful for implanting a prosthetic device in an excised annulus. The invention is especially useful for implanting a prosthetic heart valve, and is therefore described below with respect to such an application. The invention also relates to a surgical method for implanting prosthetic devices, particularly heart valves.

The surgical replacement of a defective heart valve has become a widely practiced surgical operation. In such a surgical operation, the defecting valve is surgically removed, and a bio or mechanical prosthetic valve is implanted in the excised annulus by a plurality of sutures, usually varying from 12–20, depending upon the size of the excised annulus. Such a surgical operation involves cardiopulmonary bypass circulation and cardiac arrest. The longer the period of cardiac arrest, the greater the danger of post-operative complications. Many implements have been proposed for use in such a surgical operation in order to shorten the period of cardiac arrest. Examples of the known devices are described in U.S. Pat. Nos. 4,185,636, 4,492,229, 4,932,965, and U.S. Pat. NO. 4,702,250 of which I am a joint inventor. However, insofar as I am aware, none of these previously known devices has found widespread use.

OBJECTS AND BRIEF SUMMARY OF THE INVENTION

An object of the present invention is to provide a novel surgical implement particularly useful for implanting a prosthetic device, especially a prosthetic heart valve, having advantages over the previously known implements including that of the above-cited U.S. Pat. No. 4,702,250, as will be described more particularly below. Another object of the invention is to provide a novel surgical method for implanting prosthetic devices especially valves.

According to a broad aspect of the present invention, there is provided a surgical implement particularly useful for implanting a prosthetic device in an excised annulus by means of a plurality of sutures, comprising: a manually grippable handle; and a suture retainer carried by the handle constructed for receiving and releasably retaining a plurality of sutures; the suture retainer including an outer annular face divided by visually discernible dividers into a plurality of divisions, each division including a space between two adjacent dividers having retainers for receiving and releasably retaining the two opposite ends of at least one suture to be applied, to facilitate the application and uniform spacing of the sutures.

According to further features in the described preferred embodiments, each division includes at least two slits for receiving and releasably retaining the opposite ends of the respective suture to facilitate identifying and tying the opposite ends. Preferably, each division includes at least four slits to allow the application of at least one additional suture at the respective division and at the option of the surgeon, as well as to facilitate the application of the sutures without precisely aiming them within the respective division when applying the sutures to the suture retainer. Each of the slits preferably has opposed, converging, yielding surfaces for receiving and releasably retaining sutures of different thicknesses.

According to further features in the described preferred embodiment, the annular array of slits is defined by a coiled spring supported in an annular configuration around the outer annular face of the suture retainer for receiving and releasably retaining sutures between selected coils of the spring, the coiled spring including a plurality of coils in each of the divisions. While such a construction is particularly advantageous, other constructions, such as plastic discs having a slitted outer annular surface, or plastic rods supported in an annular shape and having a slitted outer surface, could also be used.

According to a further feature in the described preferred embodiments, the annulus is to be excised in a predetermined non-circular shape according to the shape of the prosthetic device to be implanted, and the outer face of the suture retainer includes a visually discernible representation of the general shape of the excised annulus. This facilites optimum spacing of the sutures with respect to the excised annulus. The preferred way of accomplishing this is to make the outer annular face of the suture retainer of generally the same shape as that of the annulus to be excised; preferably, however, it is of larger size to facilitate handling the sutures, but may also be of smaller size to minimize obstructing the surgical site.

Embodiments are also described including an illuminating device for artificially illuminating the working area.

Such an implement is especially useful for implanting prosthetic valves and provides a number of important advantages when so used, as more particularly described below.

According to a still further aspect of the present invention, there is provided a quick and efficient method of implanting a prosthetic device, particularly a prosthetic valve, permitting the simultaneous suturing of the excised annulus and sewing ring with pledgeted double-armed sutures in the mattress fashion.

BRIEF DESCRIPTION OF THE DRAWINGS

The invention is herein described, by way of example only, with reference to the accompanying drawings, wherein.

DESCRIPTION OF PREFERRED EMBODIMENTS

The surgical implements illustrated in the drawings are for implanting a prosthetic aortic or pulmonic valve, which involves making an excised annulus of generally curved triangular shape. Thus, FIG. 1 pictorially illustrates at 2 the diseased valve to be replaced, at 3 the excised annulus of curved triangular configuration prepared by the surgeon after removing the defective valve and preparing the site for implanting the prosthetic valve, and at 4 the prosthetic valve to be implanted in the excised site 3. Such a valve is normally provided with a sewing ring 5 for receiving the sutures 6 used in implanting the prosthetic valve in the excised annulus 3.

Figure 1:
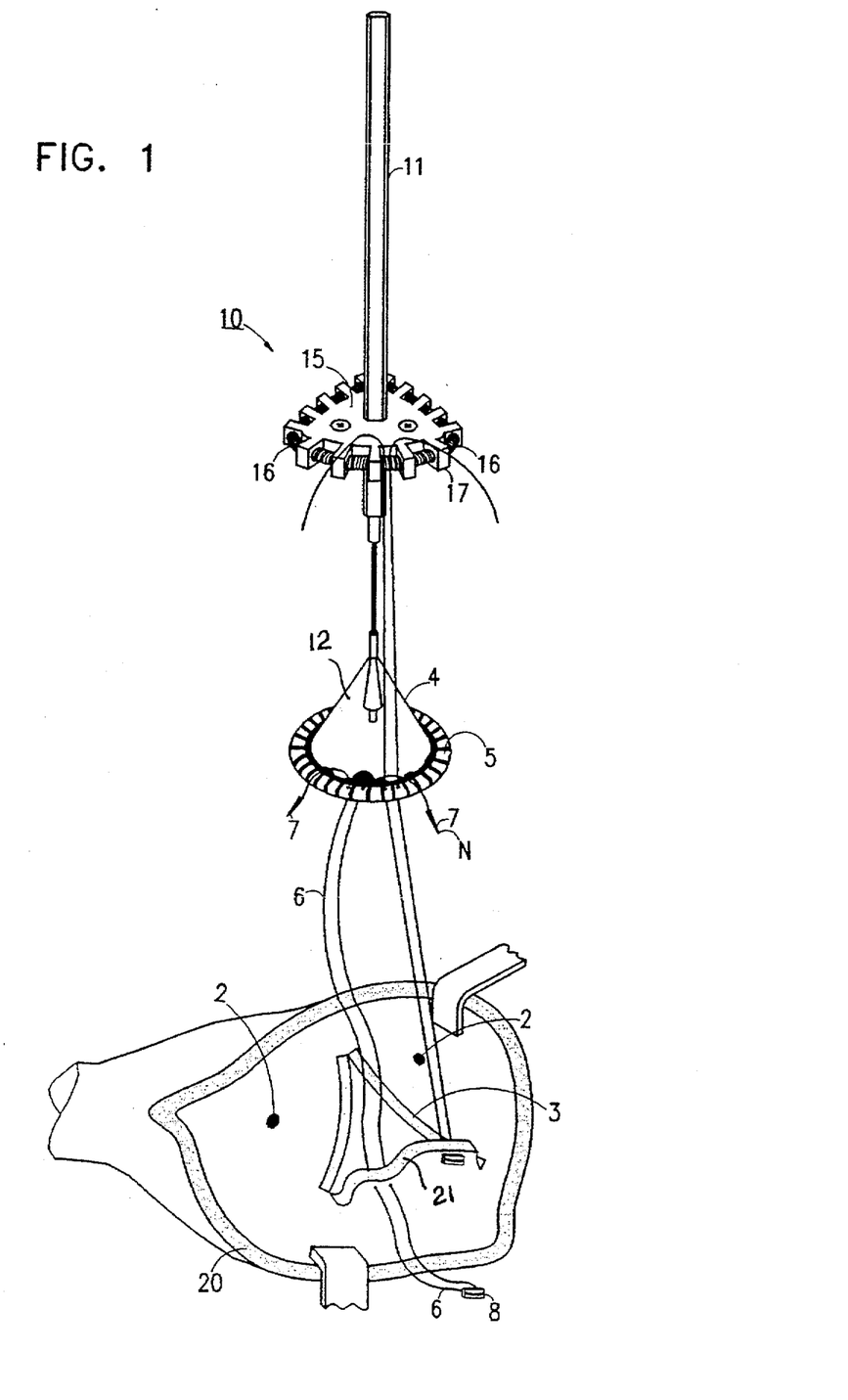
FIG. 1 is a three-dimensional view illustrating of one form of surgical implement constructed in accordance with the present invention.

As will be described more particularly below, each suture 6 is a double-armed suture; that is, it carries a needle 7 at each of its two opposite ends for surrounding tissue at the excised annulus 3 and through the sewing ring 5 of the prosthetic valve 4. Each suture is also provided with a pledger 8, e.g., of "Teflon"(Reg. T.M.), in order to increase the surface contact between the suture and the tissue receiving it at the excised annulus.

The surgical implement illustrated in FIG. 1 is generally designated 10. It includes a manually grippable handle 11 and a valve holder 12 for releasably holding the prosthetic valve 4. Any known type of valve holder may be used for this purpose, for example as described in the above-cited U.S. Pat. No. 4,702,250.

The surgical implement in FIG. 1 further includes a suture retainer, generally designated 15, carried by the handle 11 preferably at the distal part of the handle close to the prosthetic valve. A coiled spring 16 is supported around the outer annular face of the suture retainer 15, for receiving and releasably retaining the sutures 16 between selected coils of the spring. For this purpose, suture retainer 12 is integrally formed with a plurality of spaced ribs 17 having openings 18 for receiving the coiled spring 16.

Figures 2, 4:
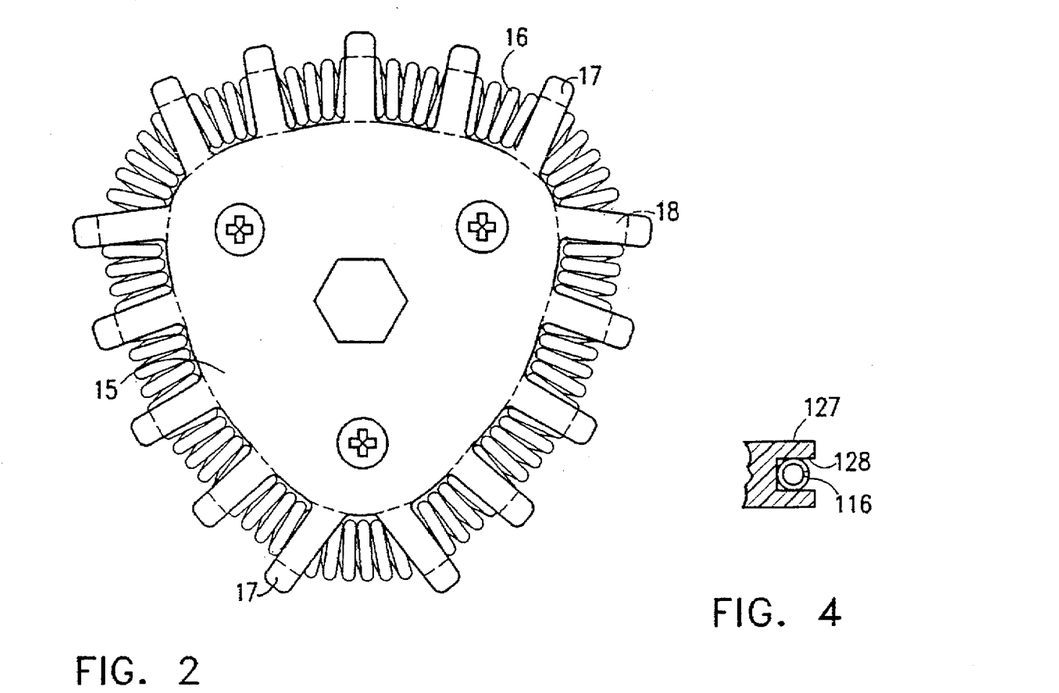
FIG. 2 is a top plan view illustrating the suture retainer in the implement of FIG. 1.
FIG. 4 is a partial sectional view illustrating a modification in the construction of the suture retainer of either FIGS. 1 or 2.

The coiled spring 16, as shown in FIG. 2, is made of wire of circular cross-section coiled into a helix and supported in an annular configuration around the outer annular face of the suture retainer 15. The coiled spring is applied under light traction so that when supported in the illustrated curved configuration, the coils are lightly pressed together in the inner face of the spring, and tend to spread apart slightly in the outer face. The coiled spring thus forms an annular array of slits having opposed, yielding surfaces for receiving and releasably retaining the sutures. The circular cross-section of the wire used for making the coiled spring results in the outer surfaces defining the slits diverging in the outward direction, thereby facilitating the insertion of the sutures between the coils.

As described earlier, the outer shape of suture retainer 15 is generally the same as the excised annulus 3 prepared by the surgeon for implanting the prosthetic valve 4. In the example illustrated in FIGS. 1 and 2, the defective valve to be replaced is an aortic valve, which involves excising an annulus 3 of generally curved triangular configuration. Therefore the configuration of the surgical suture retainer 15 is also of generally the same curved triangular shape as the excised annulus 3.

The ribs 17, besides holding the coiled spring 16 in an annular configuration on the outer face of the suture retainer 15, also serve as visually discernible dividers dividing the outer annular face of the suture retainer into a plurality of divisions, one for each of the sutures to be applied. For example, in the prosthetic valve illustrated in FIG. 1, normally fifteen sutures would be used, and therefore there would be fifteen ribs 17 dividing the outer surface of the suture retainer into fifteen divisions, one for receiving each of the fifteen sutures. Each of the fifteen divisions defined by the ribs 17 accommodates at least two coils of the coiled spring 16 to facilitate receiving, identifying, and tying the opposite ends of the suture to be received in the respective. Preferably, however, there are more than two coils, e.g., four or five coils, in each division. This facilitates the application of the sutures by the surgeon without requiring the surgeon to precisely aim the suture with respect to the suture holder. It also gives the surgeon the option of adding an additional suture or two at any location of the excised annulus should this appear to be necessary or desirable during the course of the surgical operation.

While the suture retainer 15 is of generally the same external shape as the excised annulus 3, it is may be of larger size to facilitate handling and proper placement of the sutures in their respective locations. However, the suture retainer 15 may also be of smaller size, and/or may be of transparent plastic, to minimize obstruction with the surgical site.

The surgical implement illustrated in FIGS. 1 and 2 may be used in the following manner for replacing a defecting aortic valve.

The chest is opened by a midsternotomy, and a cardiopulmunary bypass is established by cannulation of the aortic root and the right atrium. The aorta is then cross-clamped, and cardioplegia is injected in order to arrest the heart. The aortic root is opened via an S-shaped incision, pictorially illustrated at 20 in FIG. 1, the defective aortic valve 2 is excised, and an excised annulus 3 of generally curved triangular configuration is prepared for receiving the prosthetic valve 4.

The surgical implement 10 is preloaded with the prosthetic valve 4 but not with the sutures 6 to be used in the implanting. Rather, it is equipped with a suture retainer 15 of appropriate configuration (in this case curved triangular configuration) coresponding to the excised annulus 3 to receive the prosthetic valve. Each of the sutures 6 carries a needle 7 at each of its opposite ends, and a pledger 8 at the location, or slidable to the location, of contact of the suture with the tissue around the excised annulus.

The stitching is started by passing the needle 7 at one end of the first suture 6 through the non-coronary cusp rim 21 and then through the sewing ring 5 of the prosthetic valve 4. That end of the suture is then inserted between a pair of coils of the spring 16 at the division allocated to that suture between the ribs 17. The suture is slightly tensioned, and is releasably retained under this tension by the coils of the spring. The needle is then cut away from the respective end of the suture leaving an excess of the suture at that end.

The other end of the same suture is then applied in the same manner and is inserted between a pair of coils adjacent to the one receiving the first-mentioned end in the same division defined by the ribs 17. The needle at that end is also cut away leaving an excess of the suture at that end.

The coils of spring 16 releasably retain both ends of the suture such that handle 11 may be pulled outwardly to apply a tension to the two suture ends and also to pull out slightly the tissue engaged by the suture. The pledger 8 of the respective suture provides a large surface are of contact between the suture and the tissue, thereby permitting this tension while decreasing the possibility of tearing the tissue. If excess tension is applied to the sutures, this excess tention will be taken-up by the sliding of the sutures between the coils of the spring, thereby minimizing the risk of tearing the annulus tissue.

The other sutures 6 are then applied in the same manner, one after the other, according to the mattress techniques, i.e., from the outside to the inside. They are received between adjacent coils of the spring 16 in their respective divisions between the ribs 17 of the suture retainer 15, according to their respective locations in the excised annulus.

After all the sutures have thus been applied and their needles cut-away, handle 11 may then be moved slightly outwardly to tension all the sutures and to better expose the excised annulus. If any suture is found to be insufficiently tensioned, this can be easily corrected by merely pulling on the respective suture to apply the proper tension to it. As mentioned earlier, if excessive tension is applied to one or more of the sutures, the respective suture will merely slip between the coils of the spring, thereby reducing the risk of tearing the annulus tissue.

After the sutures have thus been applied to the excised annulus and tensioned to better expose the annulus, the prosthetic valve 4 is released from holder 12 and slid into place into the annulus. Each pair of sutures are then tied down and cut. The aortic opening is then sutured, and the aortic clamp is then released to allow the heart to resume beating.

The use of the surgical implement illustrated in FIGS. 1 and 2 thus enables a number of important advantages to be gained, as compared to the existing techniques: Thus, the novel implement enables the surgeon to select the type of suture to be used, something not permitted by pre-loading suture retainers. It also allows simultaneous suturing of the excised annulus and the valve sewing ring even when using pledgeted double-armed sutures in the mattress fashion, by far the most popular technique in present use, while minimizing wasted time caused by needle search. This enables the cardiac arrest time to be substantially reduced as compared to the present techniques using pledgeted double-armed sutures in which the excised annulus and the sewing ring are sutured separately.

The above-described implement and procedure also provides better exposure and division of the suture site to the surgeon. It also allows suture-length adjustment, prevents annular tears, retains the sutures without looping or tying, and decreases the possibility of entanglements and loose ends of the sutures as they are applied. Further, forming the annular surface of the suture retainer generally of the same configuration as the excised annulus, and dividing this annular surface into divisions according to the sutures to be applied, greatly facilitates the application of each suture to its proper location without the surgeon having to precisely aim each suture. In addition, providing each division with at least two slits aids the application, identification and tying of the opposite ends of each suture; and moreover, providing more than two slits at each division permits the surgeon to add a suture at any particular location should this appear to be necessary or desirable during the course of the operation.

All the foregoing advantages are extremely important in reducing post-operative mortality and morbidity and particularly the danger of the often-fatal post-operative paravulvular leak.

Figure 3:
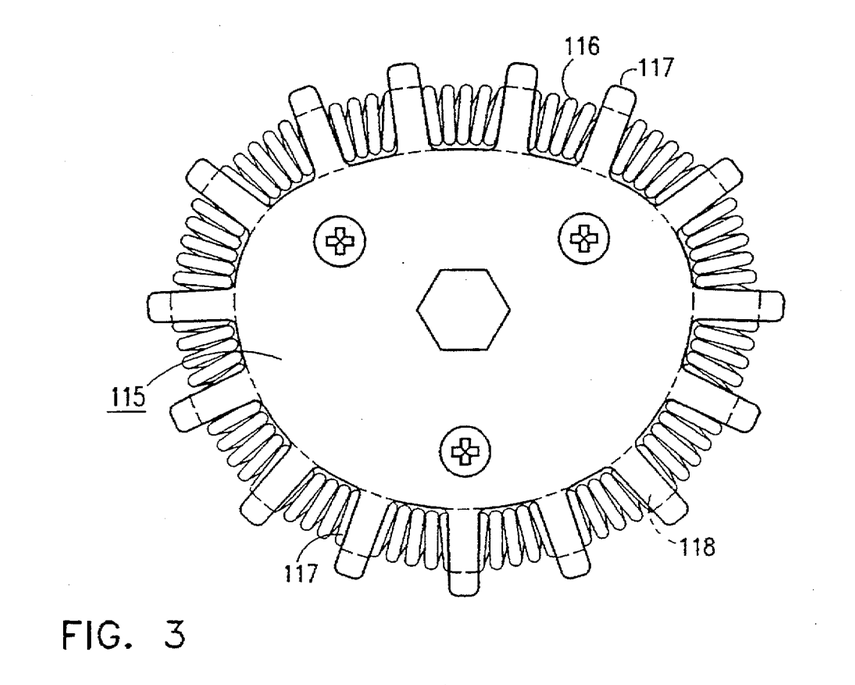
FIG. 3 is a top plan view of another type of suture retainer that may be included in the surgical implement of FIG. 1.

FIG. 3 illustrates a suture retainer for use in implanting a prosthetic valve requiring an excised annulus of a curved oval shape, such as when implanting a mitral valve or a tricuspid valve. In this case, the suture retainer, therein designated 115, would be of the same curved oval shape as the excised annulus to be prepared for the respective valve, but could be of slightly larger size to facilitate handling of the sutures, or of slightly smaller size to reduce the obstruction with the surgical site. In all other respects, the suture retainer illustrated in FIG. 3 would be incorporated in the surgical implement illustrated in FIG. 1 and would be used in the same manner as described above for implanting the prosthetic valve.

In the suture retainer 115 illustrated in FIG. 3 (as well as that illustrated in FIGS. 1 and 2), the coil spring 116 is retained in an annular configuration around the outer face of the suture retainer by being passed through holes 118 in the ribs 117 integrally formed in the suture retainer. FIG. 4 illustrates a variation wherein the ribs, therein designated 127, are provided with edge slots 128 for retaining the coiled spring in its annular configuration around the outer face of the suture retainer. Thus, the coiled spring may be formed in an endless loop and simply applied via the edge slot 128 in the ribs 127.

The use of an annularly-deployed coiled spring applied around an annular suture retainer formed with ribs as described above has been found to be particularly advantageous since such a construction defines an annular array of slits having suture-reference markings for receiving and releasably retaining the sutures. However, other suture retainer constructions could be used having these characteristics, such as a plastic disc or an annular tube or rod formed with a plurality of radially-extending slits progressing inwardly from its outer edge.

Also, while it is preferred to form the suture retainer with an outer annular face generally of the same shape as that of the excised annulus in order to facilitate optimum spacing of the sutures with respect to the excised annulus, other arrangements could be used for providing a visually discernible representation of the shape of the excised annulus. For example, the shape of the excised annulus could be drawn on the suture retainer, which may therefore be of another shape (e.g., circular shape) to facilitate optimum spacing of the sutures with respect to the excised annulus. Also, the visually discernible dividers of the outer annular surface of the suture retainer could be merely in the form of markings applied to the suture retainer, rather than ribs integrally formed with the suture retainer.

Figure 5:
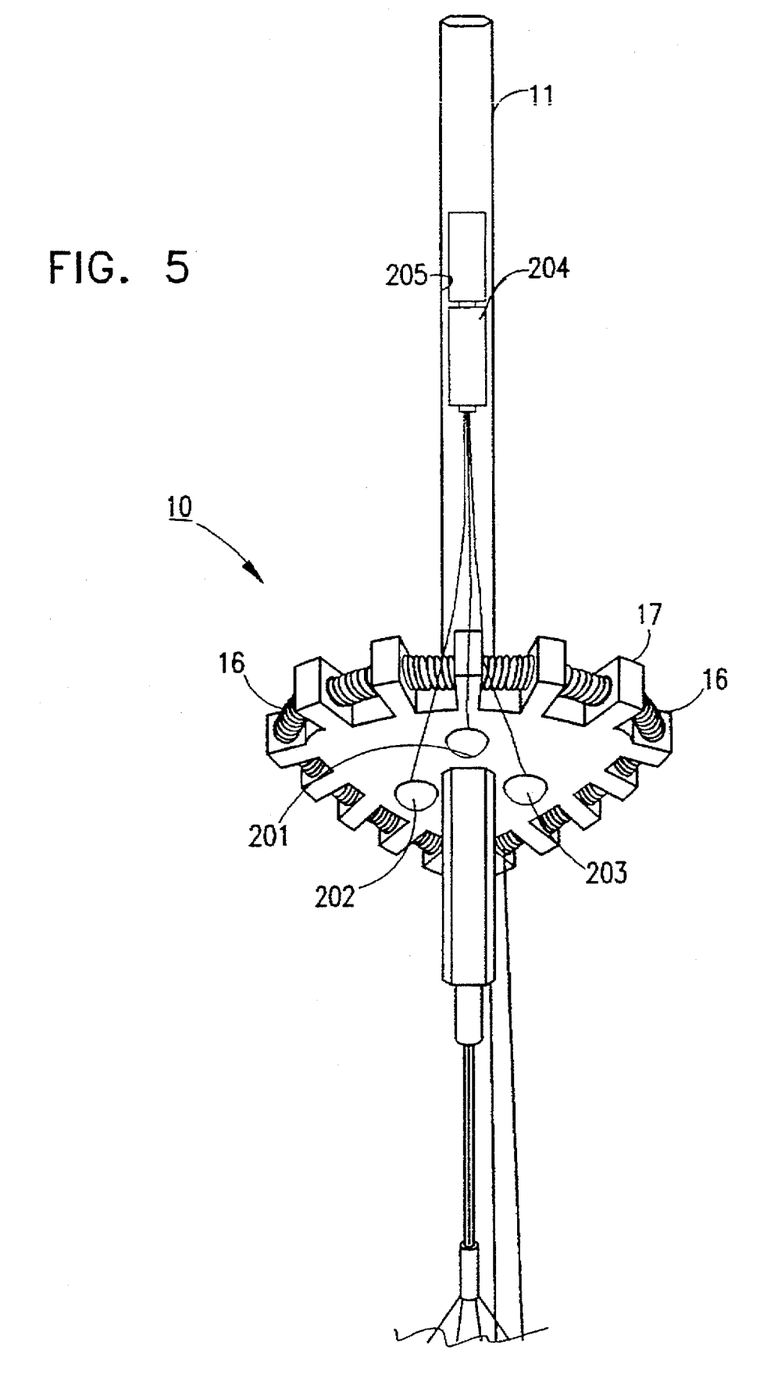
FIG. 5 illustrates another embodiment of the invention including an artificial illuminator.
Figure 6:
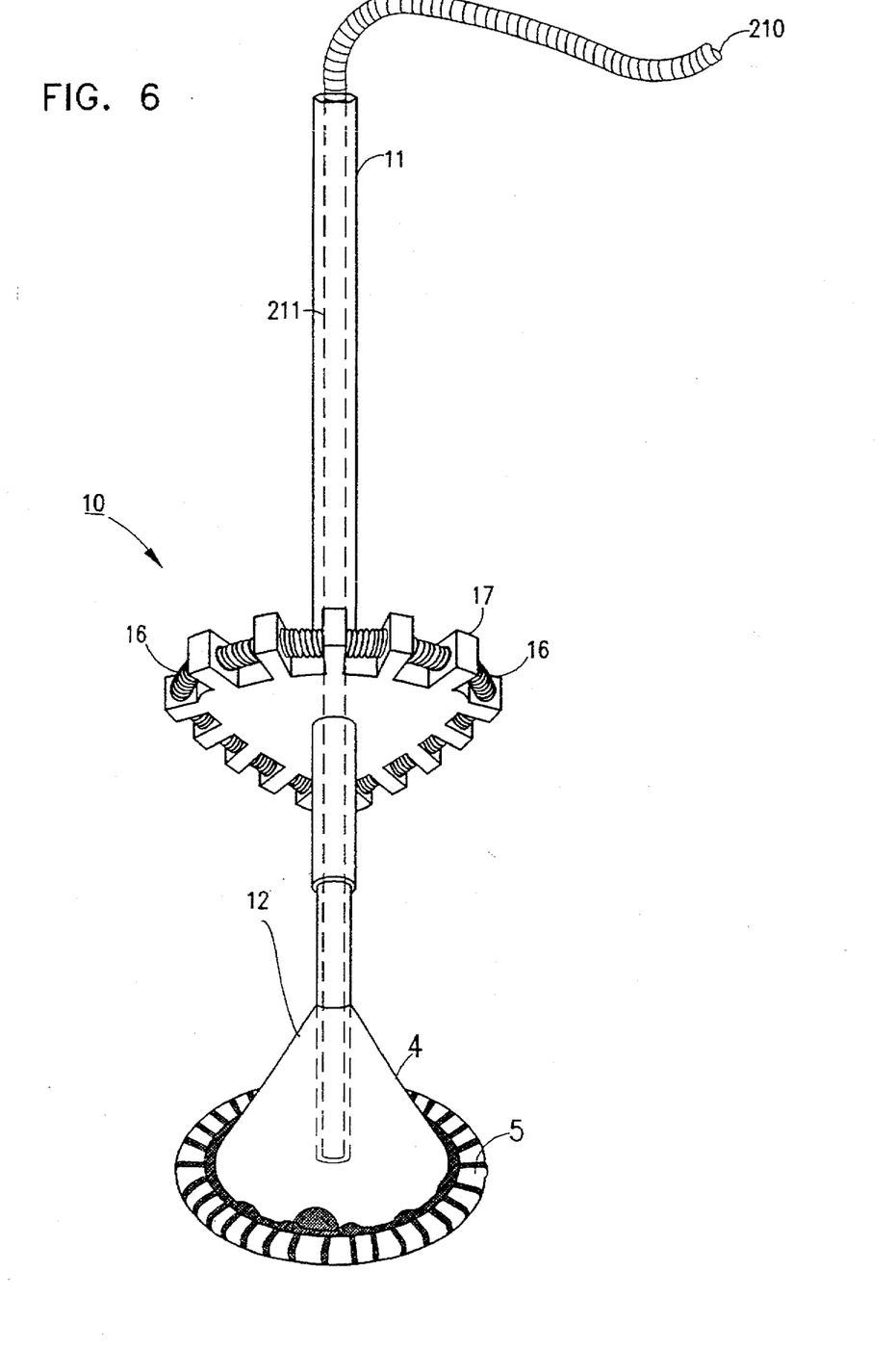
FIG. 6 illustrates a still further embodiment of the invention illustrating another type of illuminator which may be used.

FIGS. 5 and 6 illustrate implements similar to that of FIG. 1, but including an artificial illuminator for illuminating the working area. To faciliate understanding, the same reference numerals have been used in these figures as in FIG. 1 to identify corresponding elements. In the implement of FIG. 5, the suture retainer 15 is provided with three light soures 201, 202, 203 (e.g., LEDs), energized by batteries 204 within a battery compartment 205 in the handle 11, for illuminating the working area at the underside of the suture retainer. In FIG. 6, the artificial illuminator includes a light conductor in the form of an optical fiber bundle 211 within the handle 11 optically coupleable at one end to a light box (not shown), such as provided for the regular pediatric bronchoscope commonly available in operating rooms, and extending through the plastic-core type holder 4 for the prosthetic valve 5 to illuminate the working area.

While the invention is particularly useful for implanting prosthetic valves, it will be appreciated that other prosthetic devices could be implanted in an excised annulus in the manner and with the implement described above. Many other variations, modifications and applications of the invention will be apparent.

I claim:

1. A surgical implement particularly useful for implanting a prosthetic device in an excised annulus by means of a plurality of sutures, comprising:

a manually grippable handle for manually supporting the implement during use;

and a suture retainer carried by said handle constructed for receiving and releasably retaining a plurality of sutures;

said suture retainer including an outer annular face divided by dividers into a plurality of divisions, each division including a space on said annular face between two adjacent dividers having retainers for receiving and releasably retaining the two opposite ends of at least one suture to be applied, said dividers being visually discernible from said retainers for facilitating the application and uniform spacing of the sutures.

2. The implement according to claim 1, wherein each of said divisions includes at least two slits for receiving and releasably retaining the opposite ends of the respective suture to facilitate identifying and tying said opposite ends.

3. The implement according to claim 2, wherein each of said divisions includes at least four slits to allow the optional application of at least one additional suture at the respective division, as well as to facilitate the application of the sutures without precisely aiming them within the respective division when applying the sutures to the suture retainer.

4. The implement according to claim 2, wherein each of said slits has opposed, converging, yielding surfaces for receiving and releasably retaining sutures of different thicknesses.

5. The implement according to claim 2, wherein said annular array of slits is defined by a coiled spring supported in an annular configuration around the outer annular face of the suture retainer for receiving and releasably retaining sutures between selected coils of the spring, said coiled spring including a plurality of coils in each of said divisions.

6. The implement according to claim 5, wherein said dividers are ribs integrally formed with said suture retainer and projecting radially outwardly of the coiled spring.

7. The implement according to claim 1, wherein said annulus is to be excised in a predetermined non-circular shape according to the shape of the prosthetic device to be implanted, and wherein said suture retainer includes a visually discernible representation of the general shape of said annulus to facilitate optimum spacing of the sutures with respect to said annulus.

8. The implement according to claim 7, wherein the outer annular face of said suture retainer is of generally the same shape as that of said annulus.

9. The implement according to claim 1, further including an illuminating device for projecting artificial light onto the working area of said annulus.

10. An implement according to claim 1, wherein said manually grippable handle is at one side of the suture retainer, and wherein the implement carries at the opposite side of said suture retainer a valve holder adjacent to said suture retainers for releasably holding a prosthetic valve to be implanted in said excised annulus.

11. A surgical implement particularly useful for implanting a prosthetic device in an annulus to be excised in a predetermined non-circular shape according to the shape of the prosthetic device to be implanted, said implement comprising:

a manually grippable handle;

and a suture retainer carried by said handle;

said suture retainer including a visually discernible representation of the general non-circular shape of said annulus to facilitate optimum spacing of the sutures with respect to said annulus.

12. The implement according to claim 11, wherein the outer annular face of said suture retainer is of generally the same shape as that of said annulus.

13. The implement according to claim 12, wherein the size of said suture retainer is slightly larger than the size of said annulus.

14. The implement according to claim 12, wherein the suture retainer is of generally curved triangular shape for use in implanting an aortic or pulmonic prosthetic valve of generally curved triangular shape.

15. The implement according to claim 12, wherein the suture retainer is of generally oval shape for use in implanting a mitral or tricuspid prosthetic valve of generally oval shape.

16. A surgical implement particularly useful for performing a surgical operation involving the application of sutures in a working area, said implement comprising:

a manually grippable handle;

a suture retainer carried by said handle constructed for releasably retaining at least one suture;

and an illuminating device carried by said implement for projecting artificial light onto said working area while said suture retainer retains said at least one suture.

17. The implement according to claim 16, wherein said illuminating device includes a plurality of light sources carried by said suture retainer and energized by batteries located within a battery compartment in said handle.

18. The implement according to claim 16, wherein said illuminating device includes a light conductor in said handle for conducting light from a light source onto the working area of the excised annulus.

19. The implement according to claim 18, wherein said handle also carries a valve holder for holding a prosthetic valve, and wherein said light conductor penetrates said suture retainer and said valve holder.

20. The implement according to claim 16, wherein said suture retainer is constructed for releasably retaining a plurality of sutures.

21. The implement according to claim 20, wherein said handle further carries a holder for a prosthetic device to be implanted in an excised annulus.

22. The implement according to claim 21, wherein said holder is for a prosthetic valve to be implanted in said annulus.

23. A surgical implement particularly useful for implanting a prosthetic device in an excised annulus of a working area by means of a plurality of sutures, comprising:

a manually grippable handle;

a holder for the prosthetic device to be implanted in said annulus;

and an illuminating device carried by said implement for projecting artificial light onto the working area at said annulus while said suture retainer retains said prosthetic device.

24. The implement according to claim 23, wherein said implement further comprises a suture retainer carried by said handle for releasably retaining a plurality of sutures.

* * * * *

UNITED STATES PATENT AND TRADEMARK OFFICE
CERTIFICATE OF CORRECTION

PATENT NO. : 5,690,654

DATED : November 25, 1997

INVENTOR(S) : Joel OVIL

Page 1 of 2

It is certified that error appears in the above-indentified patent and that said Letters Patent is hereby corrected as shown below:

Column 2, line 1, "embodiment" should be --embodiments--.

Column 2, line 65, after "2", there should be inserted --, the site of-- .

Column 3, line 3, "site" should be changed to --annulus--.

Column 3, line 9, before "surrounding", there should be inserted --insertion through--.

Column 4, line 23, "2" should be deleted.

Column 4, line 34, "pledger" should be --pledget--.

Column 4, line 54, "pledger" should be --pledget--.

Column 5, line 60, after "reduce", "the" should be deleted.

Column 5, line 61, "with" should be --of--.

Column 5, line 67, "coil" should be --coiled--.

Column 6, line 46, after "end", there should be inserted --210--.

UNITED STATES PATENT AND TRADEMARK OFFICE
CERTIFICATE OF CORRECTION

PATENT NO. : 5,690,654

DATED : November 25, 1997

INVENTOR(S) : Joel OVIL

Page 2 of 2

It is certified that error appears in the above-indentified patent and that said Letters Patent is hereby corrected as shown below:

Column 8, line 54, "suture retainer retains" should be --holder holds

Signed and Sealed this

Twenty-seventh Day of October, 1998

BRUCE LEHMAN

Attest:

Attesting Officer

Commissioner of Patents and Trademarks